US009764136B2

(12) United States Patent
McIntyre et al.

(10) Patent No.: US 9,764,136 B2
(45) Date of Patent: Sep. 19, 2017

(54) CLINICAL DECISION SUPPORT SYSTEM

(71) Applicant: Case Western Reserve University, Cleveland, OH (US)

(72) Inventors: Cameron McIntyre, Cleveland Heights, OH (US); Reuben R. SHamir, Cleveland, OH (US); Benjamin L. Walter, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/725,484

(22) Filed: May 29, 2015

(65) Prior Publication Data

US 2015/0352363 A1 Dec. 10, 2015

Related U.S. Application Data

(60) Provisional application No. 62/008,623, filed on Jun. 6, 2014, provisional application No. 62/107,597, filed on Jan. 26, 2015.

(51) Int. Cl.
*A61N 1/00* (2006.01)
*A61N 1/36* (2006.01)
*G06F 19/00* (2011.01)
*A61N 1/05* (2006.01)

(52) U.S. Cl.
CPC ....... *A61N 1/36067* (2013.01); *G06F 19/345* (2013.01); *A61N 1/0534* (2013.01); *A61N 1/36064* (2013.01); *A61N 1/36096* (2013.01); *G06F 19/3443* (2013.01)

(58) Field of Classification Search
CPC ............. A61N 1/0534; A61N 1/36064; A61N 1/36067; A61N 1/36096; G06F 19/3443; G06F 19/345
See application file for complete search history.

(56) References Cited

U.S. PATENT DOCUMENTS

2011/0119212 A1* 5/2011 De Bruin ................. A61B 5/00
706/12
2013/0104066 A1* 4/2013 Soederstroem ..... G06F 3/04847
715/771

* cited by examiner

*Primary Examiner* — Lindsey G Wehrheim
(74) *Attorney, Agent, or Firm* — Eschweiler & Potashnik, LLC

(57) ABSTRACT

Example apparatus and methods concern a next generation clinical decision support system (ngCDSS) for the management of neurological conditions (e.g., advanced Parkinson's disease (PD)). Conventional coupled adjustment of pharmacologic therapy and stimulation parameter settings is a time-consuming process that sometimes yields sub-optimal outcomes. Example ngCDSS use a machine learning trained function that relates deep brain stimulation (DBS) parameters, medication dosages, and patient-specific pre and post operative clinical data with actual treatment outcomes for a population of previously treated patients. Example ngCDSS incorporate image-based patient-specific computer models of the estimated stimulation volume of tissue stimulated by DBS in a multi-linear regression analysis to produce a predictor function that is highly correlated with actual outcomes. Example ngCDSS facilitate predicting the outcomes of a combined pharmacologic-DBS therapy, which in turn facilitate optimizing patient-specific treatment for improved benefits with minimal adverse effects.

9 Claims, 12 Drawing Sheets

CLINICAL DECISION SUPPORT SYSTEM

CROSS-REFERENCE TO RELATED APPLICATIONS

This application claims the benefit of U.S. Provisional Patent Application No. 62/008,623 filed Jun. 6, 2014 and U.S. Provisional Patent Application No. 62/107,597 filed Jan. 26, 2015.

FEDERAL FUNDING NOTICE

The invention was made with government support under Federal Grant No. NS047388 awarded by the National Institute of Health. The government has certain rights in the invention.

BACKGROUND

Deep brain stimulation (DBS) of the subthalamic region is an effective treatment for the motor symptoms of advanced Parkinson's disease (PD). However, following surgery to implant the DBS system in the PD patient, a neurologist may be confronted with the difficult challenge of balancing the patient's drug treatment and stimulation treatment to maximize therapeutic benefit while minimizing adverse effects. Conventionally, this complex process is driven by clinical experience. Typical optimization attempts require navigating an extremely large and complex treatment parameter space. Additionally, DBS may be associated with side effects generated by the unwanted spread of stimulation to non-target regions. The spread may depend on the patient-specific location of an electrode in the brain. The relationship between DBS electrode locations and treatment outcomes is the subject of extensive study.

First generation clinical decision support systems (CDSS) that incorporate patient-specific imaging data and electrical stimulation models to help customize DBS parameter settings to the patient have been developed in the past decade. See, for example, McIntyre, C. C., Mori, S., Sherman, D. L., Thakor, N. V, Vitek, J. L.: Electric field and stimulating influence generated by deep brain stimulation of the subthalamic nucleus. Clin Neurophysiol. 115, 589-95 (2004), Butson, C. R., Cooper, S. E., Henderson, J. M., McIntyre, C. C.: Patient-specific analysis of the volume of tissue activated during deep brain stimulation. Neuroimage. 34, 661-70 (2007), and Frankemolle, A. M. M., Wu, J., Noecker, A. M., Voelcker-Rehage, C., Ho, J. C., Vitek, J. L., McIntyre, C. C., Alberts, J. L.: Reversing cognitive-motor impairments in Parkinson's disease patients using a computational modelling approach to deep brain stimulation programming. Brain. 133, 746-61 (2010). These first generation commercial DBS CDSS include, for example, Optivise by Medtronic (MN, USA) or GUIDE by Boston Scientific (MA, USA)). While these conventional CDSS systems provide guidance regarding electrical stimulation for postoperative PD patients, they ignore the pharmacology side of patient management.

BRIEF DESCRIPTION OF THE DRAWINGS

The accompanying drawings, which are incorporated in and constitute a part of the specification, illustrate various example devices, methods, apparatus and other embodiments of various aspects of the invention. It will be appreciated that the illustrated element boundaries (e.g., boxes, groups of boxes, or other shapes) in the figures represent one example of the boundaries. In some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example apparatus and methods provide a next generation clinical decision support system (ngCDSS) for the treatment of patients implanted with deep brain stimulation (DBS) systems. Examples are provided concerning the treatment of Parkinson's Disease (PD) patients. While the examples concern PD patients, example apparatus and methods are more generally applicable to patients having stimulation systems in their brains. In one embodiment, an ngCDSS facilitates selecting combinations of stimulation and medication for treating advanced PD. One example ngCDSS produces recommendations based on data concerning patient-specific PD symptoms, clinical history, levodopa equivalent daily dosage (LEDD), and the overlap between an estimated stimulation volume (ESV) of tissue stimulated by the DBS system and a therapeutic target volume. The data concerning patient-specific symptomology may include tremor, rigidity, bradykinesia, and other symptoms. More generally, example ngCDSS produce recommendations for treating a patient based on patient symptom data and patient non-symptom data.

Similarity functions trained up by machine learning algorithms may input these patient-specific details to identify clinically relevant balances between stimulation parameters and medication parameters. One example ngCDSS uses a multi-linear regression analysis that fits patient data with the actual outcome data using a linear weighted sum function. In one embodiment, the example linear weighted sum function may be produced and then manipulated (e.g., updated) using machine learning techniques that facilitate optimizing predictions for outcomes of various combinations of stimulation and medication. While a weighted sum function is described, more generally machine learning techniques facilitate manipulating functions used by an ngCDSS to predict outcomes for various combinations of stimulation and medication.

Figure 1:
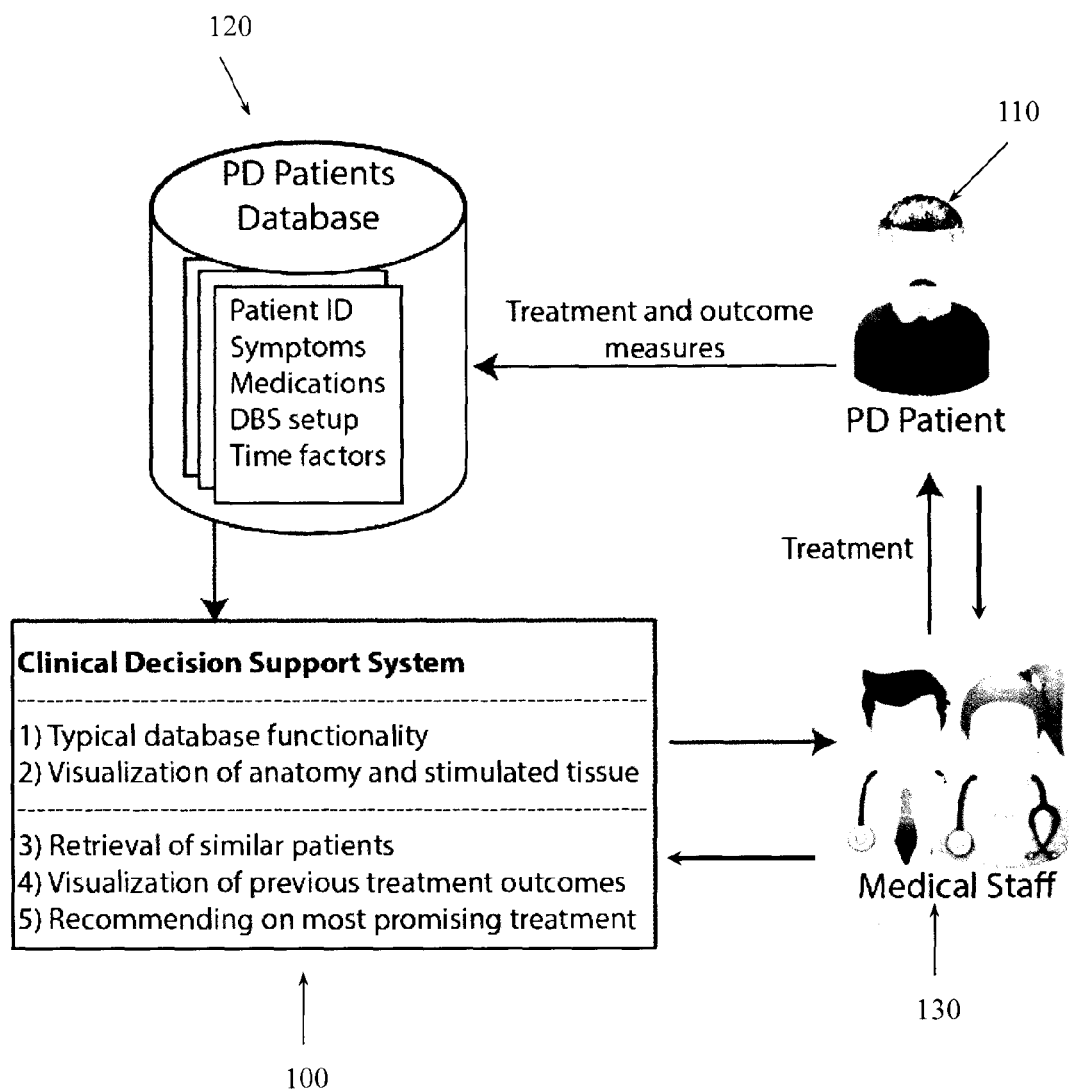
FIG. 1 illustrates an example ngCDSS.

FIG. 1 illustrates an example ngCDSS 100 that inputs data from a PD patient 110 and accesses a PD patients database 120 to make a recommendation to the medical staff 130 charged with treating the PD patient 110. While a PD patient 110 is illustrated, more generally an ngCDSS may input data from a patient and a patient database. The example ngCDSS 100 may facilitate retrieving information upon which a decision is made (e.g., similar patient data sets with respect to symptoms, time factors (e.g., age at time of surgery, time since surgery, medications, and stimulation setups)). The example ngCDSS 100 also facilitates understanding a treatment being considered by visualizing past patient outcomes. The visualization facilitates identifying results expected from different combinations of stimulation setups and drug prescriptions. The expected results can be used to make recommendations to the medical staff 130 for combinations of DBS and medication. An example ngCDSS 100 may use similarity functions that are trained up and optimized using machine learning methods derived from correlation and regression analyses. A properly trained ngCDSS that is provided with patient-specific details may recommend combinations of DBS parameter settings and medication parameters that facilitate improving the clinical management of patients including PD patients. A production ngCDSS may be updated with retrospective and/or prospective data to improve the performance of the ngCDSS.

Figure 2:
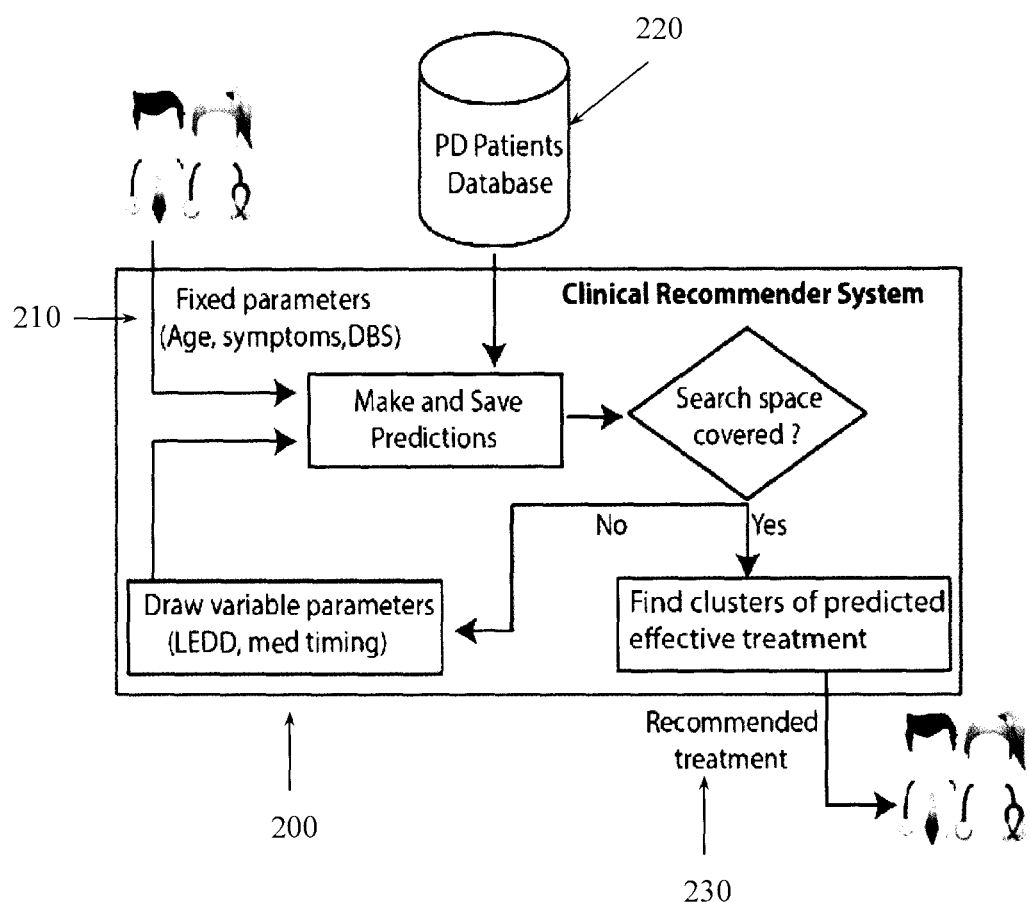
FIG. 2 illustrates an example ngCDSS.

FIG. 2 illustrates another example ngCDSS 200. A clinician enters the patient's known information 210 (e.g., age, symptoms) at the time of a postoperative visit. In one embodiment, theoretically optimal DBS parameter settings have already been defined via, for example, existing clinical tools (e.g., GUIDE DBS). In another embodiment, the DBS parameters can be incorporated as additional variables in the system. Treatment parameters including, for example, LEDD and medication intake times, may be randomly drawn and a prediction of outcomes is computed. Once the treatment parameters space is covered with a threshold number of samples selected from the PD patients database 220, clusters of predicted effective treatments are computed and recommended at 230.

ngCDSS 100 and ngCDSS 200 may be programmed to perform a method for selecting treatment parameters. For example, ngCDSS 100 and ngCDSS 200 may control a computer to input data about a patient implanted with a DBS system. The data may include imagery data, symptom data, and treatment data. ngCDSS 100 and ngCDSS 200 may also control a computer to determine an overlap between an ESV in the patient brain and a target stimulation area (TSA) in the patient brain. ngCDSS 100 and ngCDSS 200 may also select DBS parameters for the patient and medication for the patient based on correlations between the patient and other patients that had desirable therapeutic outcomes. For a PD patient, the correlations may concern relative pre-operative response to levodopa, relative post-operative change in LEDD, and the overlap. For other patients, other correlations may be considered.

Validating example apparatus and methods included receiving data from PD patients that underwent bilateral DBS placement in the subthalamic nucleus. Details of example patients are presented in Table 1. In Table 1 age refers to the patient's age at the time of the DBS surgery. The unified Parkinson's disease rating scale, part III (UPDRS-III) preoperative scores are also presented.

TABLE 1

| Patient # | Sex (M/F) | Age (years) | Follow up #visits | Follow up #months | Preoperative UPDRS-III off meds. |
|---|---|---|---|---|---|
| 01 | M | 68 | 13 | 55 | 35 |
| 02 | F | 63 | 3 | 13 | 48 |
| 03 | F | 74 | 10 | 47 | 54 |
| 04 | M | 71 | 9 | 27 | 22 |
| 05 | M | 53 | 11 | 21 | 39 |
| 06 | M | 54 | 14 | 35 | 23 |

Other data sets from other patient populations were also employed during training and validation of example ngCDSS. For example, table 2 illustrates another example data set.

TABLE 2

| Patient # | Sex (M/F) | Age (years) | Follow up #visits | Follow up #months | Preoperative UPDRS-III off meds. |
|---|---|---|---|---|---|
| 1 | F | 64 | 3 | 13 | 33 |
| 2 | M | 38 | 10 | 24 | 17 |
| 3 | F | 74 | 10 | 47 | 31 |
| 4 | F | 71 | 10 | 20 | 25 |
| 5 | M | 63 | 20 | 38 | 20 |
| 6 | M | 71 | 9 | 27 | 9 |
| 7 | M | 63 | 6 | 7 | 31 |
| 8 | F | 54 | 4 | 6 | 17 |
| 9 | M | 64 | 26 | 54 | 13 |
| 10 | M | 69 | 8 | 19 | 12 |

Example ngCDSS were provided with results from these types of patients and after machine learning were able to accurately predict motor improvement scores observed one year after surgery. In one example ngCDSS, measures of medication dosages, time factors, and symptom-specific pre-operative responses to levodopa significantly correlated with post-operative outcomes ($p<0.05$) and the effects on outcomes was of similar magnitude to that of DBS.

The third subsection of the unified PD rating scale (UPDRS-III; range 0-108) is the motor score. In the motor score, larger scores represent worse symptoms. The motor score was assessed preoperatively both off (>12 hours) and on dopaminergic medication. Postoperatively, UPDRS-III was assessed at follow-up visits of the patients. The visits were conducted under setups including: 1) on-meds on-stimulation; 2) on-meds off-stimulation; 3) off-meds on-stimulation, or 4) off-meds off-stimulation. In one embodiment, the relative improvement of motor symptoms on-medication in the preoperative state, and on/off-medication on/off-stimulation in the postoperative state were defined as follows to avoid false correlations that may arise using the non-normalized UPDRS scores:

$$100 \times \frac{PRE_{off} - PRE_{on}}{PRE_{off}} \quad [1a]$$

and $$100 \times \frac{PRE_{off} - POST_{comb}}{PRE_{off}} \quad [1b]$$

where $PRE_{off}$ is the UPDRS-III score preoperative off-medication, $PRE_{on}$ is the UPDRS-III score preoperative on-medication, and POST$_{comb}$ is the UPDRS-III score for postoperative combination of on/off-medication and on/off-stimulation.

To compare specific symptom relative improvement using equations 1a and 1b, different subsections of the UPDRS-III (motor) section were investigated. The different subsections included speech (section 18, max4), tremor (sections 20-21; max 28), rigidity (section 22, max 20), limb bradykinesia (sections 23-26, max 32), and axial akinetic symptoms (sections 19 and 27-31; max 24).

LEDD was computed from patients' medication records and the relative change in LEDD was defined as:

$$100 \times \frac{LEDD_{pre} - LEDD_{post}}{LEDD_{pre}} \quad [2]$$

where
LEDD$_{pre}$ represents the LEDD before surgery, and
LEDD$_{post}$ represents the LEDD after surgery.

Example ngCDSS rely on patient-specific DBS computer models that document anatomical locations of DBS electrodes in the patient brain as well as the stimulation volume generated by their clinically defined stimulation parameter settings. In one embodiment, creating the patient-specific DBS models included integrating MRI and/or CT data with intraoperative microelectrode recoding data to characterize the patient anatomy. The location of a DBS electrode may be identified in a postoperative CT. The electrode position used in the patient DBS model may be computed from the CT image. In different embodiments, the location of the DBS electrode may be made with or without data from an intraoperative microelectrode recording.

In one embodiment, an MRI size may be, for example, 256×256×190 with a voxel size of 1×1×1 mm³. A CT image size may be, for example, 512×512×40 with a voxel size of 0.36×0.36×2.4 mm³. Other MRI and CT image sizes may be employed. MRI-CT registration may be performed using, for example, 3D-Slicer (see, e.g., Fedorov, A., Beichel, R., Kalpathy-Cramer, J., Finet, J., Fillion-Robin, J.-C., Pujol, S., Bauer, C., Jennings, D., Fennessy, F., Sonka, M., Buatti, J., Aylward, S., Miller, J. V, Pieper, S., Kikinis, R.: 3D Slicer as an image computing platform for the Quantitative Imaging Network. Magn Reson Imaging. 30, 1323-41 (2012)). Atlas/MRI fitting, 3D electrode-model fitting and computation of ESVs and their overlap with the TSA may be performed using, for example, Cicerone (see, e.g., Miocinovic, S., Noecker, A. M., Maks, C. B., Butson, C. R., McIntyre, C. C.: Cicerone: stereotactic neurophysiological recording and deep brain stimulation electrode placement software system. Acta Neurochir Suppl. 97, 561-7 (2007)).

This patient-specific anatomical model may then be coupled with an electrical model that estimates the ESV. The ESV is a metric that estimates the spatial extent of axonal activation generated by DBS for a given parameter setting. Different brain hemispheres of different DBS patients have unique electrode placements relative to the neuroanatomy. Different brain hemispheres of different DBS patients also have unique stimulation parameter settings selected from a large number of possible options. Detailed patient-specific DBS models exist to account for these variables between patients. Example ngCDSS may rely on a single common metric to compare patients and simplify analysis.

In one embodiment, the single common metric concerns the overlap of the ESV for a specific stimulation parameter setting with the TSA. The TSA is defined to cover most ESV that are associated with effective DBS outcomes and is not limited to a specific anatomical structure. The TSA may be defined relative to the Harvard-Oxford brain atlas with representation of the subthalamic nucleus or other areas. In one embodiment, the TSA location is derived empirically from existing data. In different embodiments, the TSA may intersect the zona incerta, the globus pallidus, the pedunculopontine nucleus, or other areas. In one embodiment, the TSA may be an ellipsoid that intersects the dorsal area of the subthalamic nucleus (STN) and the zona-incerta.

Figure 3:
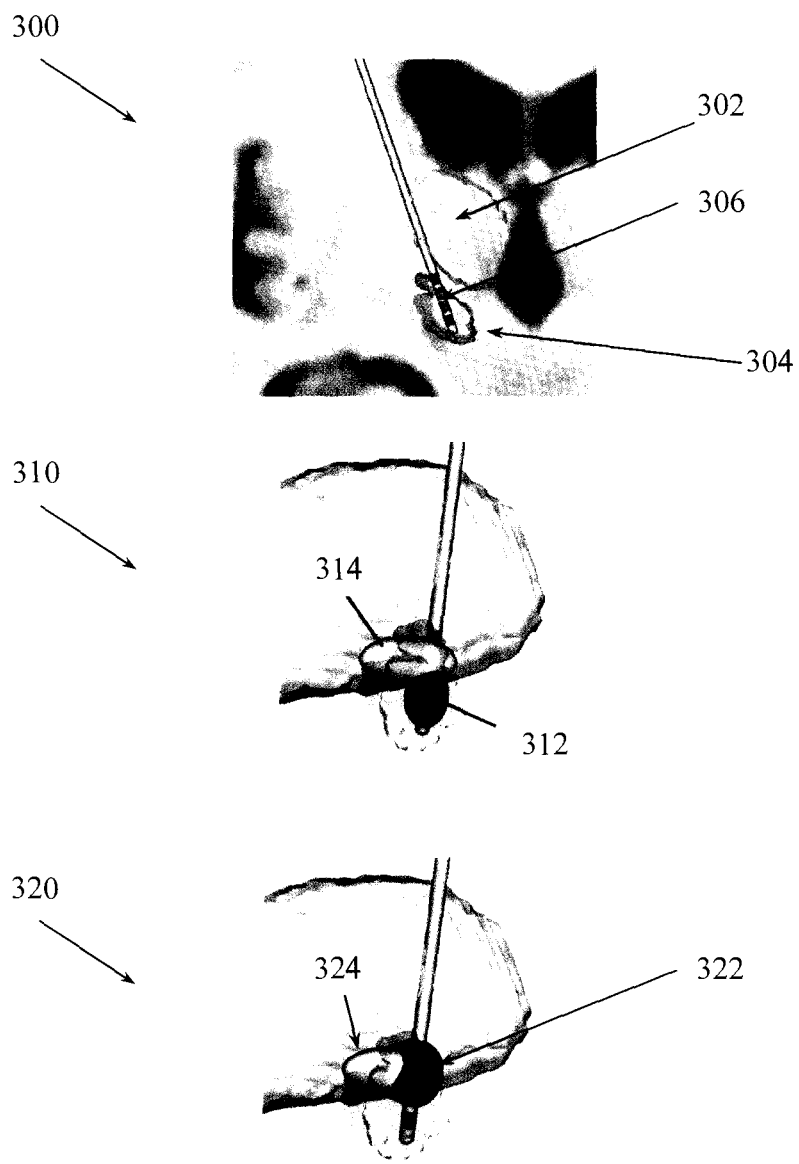
FIG. 3 illustrates structures associated with an example estimation of DBS treatment efficacy.

FIG. 3 illustrates images associated with estimating the efficacy of DBS treatment. In MRI 300, the thalamus 302 and subthalamic nucleus 304 are presented. The location of an electrode 306 is identified on a postoperative CT image and the location is transformed to MRI coordinates. Then, for different stimulation setups, such as the setups shown in example 310 and 320, an estimated volume of tissue stimulated 312, 322 may be computed and compared with a preferred therapeutic target area 314, 324. Setups that are associated with a small overlap (e.g., 312 and 314) are in general less effective in comparison to setups that yield large overlap (e.g., 322, 324).

Figure 4:
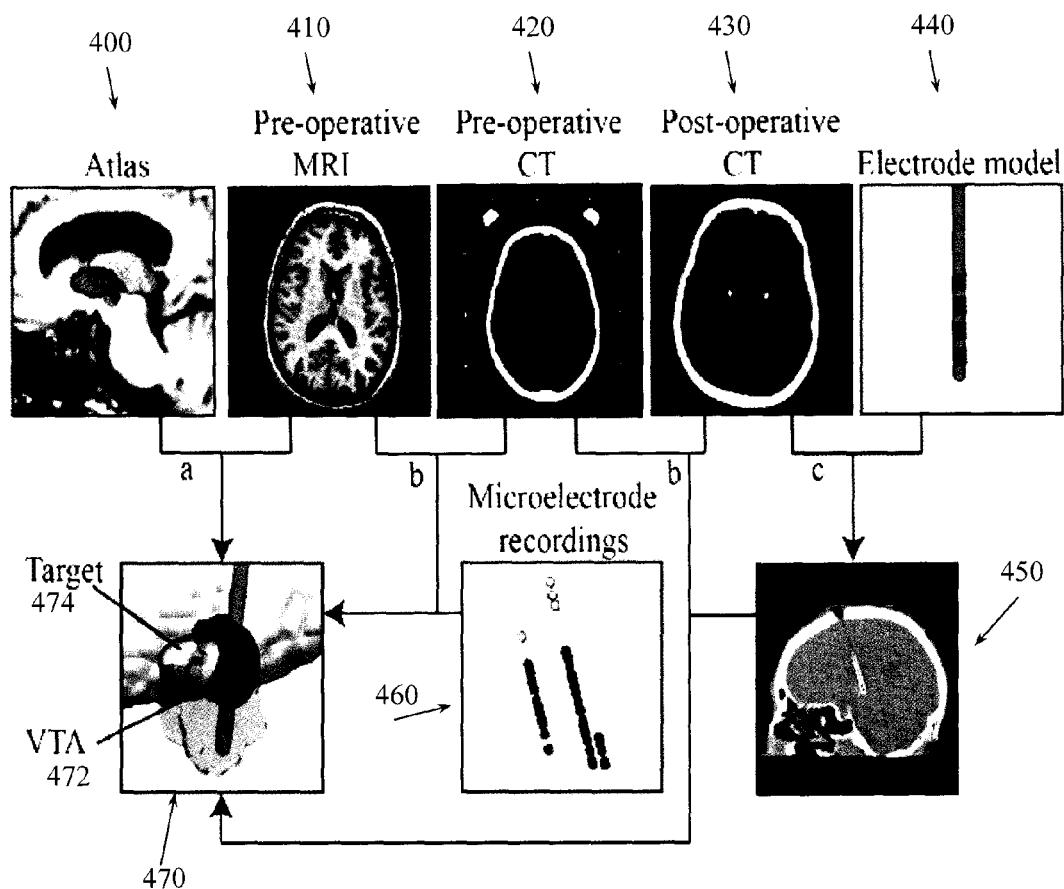
FIG. 4 illustrates processing associated with computing an estimated stimulation volume (ESV) of tissue stimulated with respect to a preferred target stimulation area (TSA).

FIG. 4 illustrates images and actions that may be performed to estimate an ESV with respect to a TSA. The estimation process may include co-registration of the patient's preoperative MRI 410 with a brain atlas 400. The computation may also include co-registration of the patient's preoperative MRI 410 and postoperative CT 430 to the preoperative CT 420 with the stereotactic frame. This registration establishes a common coordinate system. An electrode model 440 may also be included. For example, the computation may also include defining the DBS electrode position 450 relative to intraoperative microelectrode recordings 460 and the anatomical volumes, although this step may be optional. The computation may produce a visualization like that illustrated in 470, which facilitates understanding the overlap between the ESV 472 and the target 474.

In one embodiment, the midline, anterior commissure (AC), and posterior commissure (PC) are identified on a patient's pre-operative MRI and on an atlas image. A rigid transformation is computed to match the defined AC/PC and midline axes of the atlas with the patient MRI. The atlas anatomical volumes, including the TSA, are overlaid on the patient MRI and fitted to the anatomy. The fitting may be performed using, for example, a three dimensional (3D) affine transformation that uses for example, three translation parameters, three rotation parameters, and three scaling parameters.

A patient-specific model is constructed within the context of a stereotactic coordinate system. In one embodiment, the stereotactic coordinate system facilitates incorporating intraoperative microelectrode recording (MER) data defining the location of neurons (e.g., STN neurons). While MER data is defined, more generally, electrode locating information is acquired. In one embodiment, upon detecting a misalignment of atlas volumes fitted to the anatomy and the electrode locating information points, a linear translation of the atlas volumes may be performed to produce a better correspondence with the electrode locating information.

The ESV may be computed from stimulation settings identified during postoperative follow-up visits. The volume of the overlap between the ESV and the TSA is computed. The percentage of the volume of the overlap from the total volume of the target may be defined as:

$$100 \times \frac{|\text{target\_zone} \cap ESV|}{|\text{target\_zone}|} \qquad [3]$$

where:

target zone is the preferred stimulation area,

ESV is the computed zone of tissue stimulated, and

|x| denotes the volume of x.

The average of the right and left overlap volumes may be computed to represent a single measure for the clinical visit of the patient. Values for the simplified single metric may then be used to identify similar patients.

More generally, the following actions may be performed to identify the volume of overlap between the ESV and the TSA.

1) The anatomical atlas, with target volume, is registered to the patient's preoperative MRI;
2) a 3D geometrical model of the implanted electrode is fitted to its postoperative CT image counterpart;
3) the CT image is registered to the MRI and the 3D electrode model is transformed to MRI coordinates;
4) For different DBS parameter setups, an ESV is computed around the electrode with a validated method that incorporates an artificial neural network to model the spread of stimulation;
5) The volume of the overlap between the ESV and the TSA is computed and the percentage of the volume of the overlap from the total volume of the TSA is computed.

Figure 7:
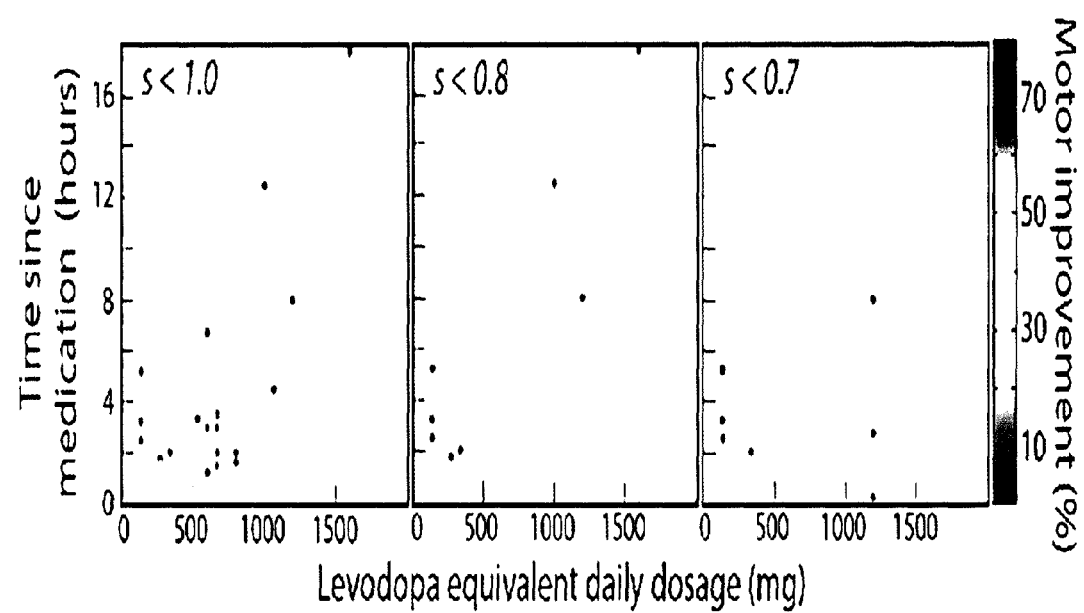
FIG. 7 illustrates a visualization of treatment outcomes.

Example ngCDSS employ a metric that measures the similarity between patients with respect to their PD symptoms, clinical history, LEDD, and the delivery timing of the LEDD. More generally, example ngCDSS employ a metric that measures the similarity between a patient with respect to their symptoms, clinical history, and medications. These similarities may be viewed in light of the overlap between the ESV and the predefined therapeutic target volume. In one embodiment, the overlap itself may be used as a metric for correlations. The similarly metric facilitates retrieving relevant data (e.g., office visit charts) from other patients, which in turn facilitates providing a retrospective reference for visualization of treatment outcomes. FIG. 7 illustrates one example visualization of treatment outcomes of previous patients with respect to a simulated new patient. The example summarizes the outcomes as a function of LEDD and of its timing. Three thresholds for the similarity measure s were applied (1.0, 0.8 and 0.7), where a smaller s corresponds to greater similarity within the database.

Reading and extracting relevant information from patient charts may be difficult. Example ngCDSS facilitate presenting a visual summary of relevant patient information upon which decisions may be made. FIG. 7 provides an example visualization of data for a hypothetical new patient with median feature values of age 64, 12 months since surgery, preoperative motor response to levodopa of 61%, preoperative levodopa dosage of 1660 mg, and ESV/TSA overlap of 20%. FIG. 7 illustrates two dimensional (2D) projections of data from previous patients with various levels of similarity to the hypothetical new patient. The results illustrate that similar patients responded well with low LEDD of 300-400 mg/day in combination with DBS compared to higher LEDD dosages. The results also illustrate that motor improvement lasted approximately four hours per dose. While results concerning LEDD are provided, more generally, example ngCDSS may facilitate visualizing combinations of stimulation parameters and medications.

In one embodiment, features that were selected for retrieving data from similar patients were normalized by computing their Z-score over postoperative visits. In one embodiment, the Z-score was computed using:

$$Z_{pi} = \frac{(x_{pi} - \mu(x_{pi}))}{\sigma(x_{pi})} \qquad [4]$$

where:

the index i enumerates features including, for example, improvement in symptoms;

the index p enumerates different postoperative office visits;

$x_{pi}$ is a vector of selected feature values;

$\mu(x_{pi})$ is the mean of $x_{pi}$; and $\sigma(x_{pi})$ is the standard deviation of $x_{pi}$.

A normalized signature vector $Z_p = (zp_1 \ldots zp_n)$ may be defined for the postoperative visits of PD patients. The similarity between two postoperative visits may be defined as the root mean square (RMS) between computed signatures according to:

$$\text{similarity}(Z_p, Z_q) = \sqrt{\frac{\sum_{i=1}^{n}(Z_{pi} - Z_{qi})^2}{n}} \qquad [5]$$

In one example ngCDSS, this similarity measurement may be used to identify previous patients with common features. From the patients with common features, combinations of DBS parameters and medications that produced favorable outcomes can be identified. For example, when a patient presents following DBS surgery seeking optimization of their outcome by manipulating DBS and medication, the known parameters may be input into the ngCDSS for the patient to start the process. The ngCDSS may compute the patient's signature Z-vector from the known parameters. The ngCDSS may then compute the similarity between the patient's signature Z-vector and stored Z-vectors. Stored Z-vectors that fall within a threshold value may then be used to retrieve previous patient data and outcomes. A prescription for a combination of DBS parameters and medications may then be produced based on the outcomes for the similar patients. In one embodiment, stored z-vectors may be examined to identify clusters of treatment parameters associated with desired outcomes. The ngCDSS or physician may then select treatment options based on the outcomes produced by previous treatment of similarly situated patients.

Figure 5:
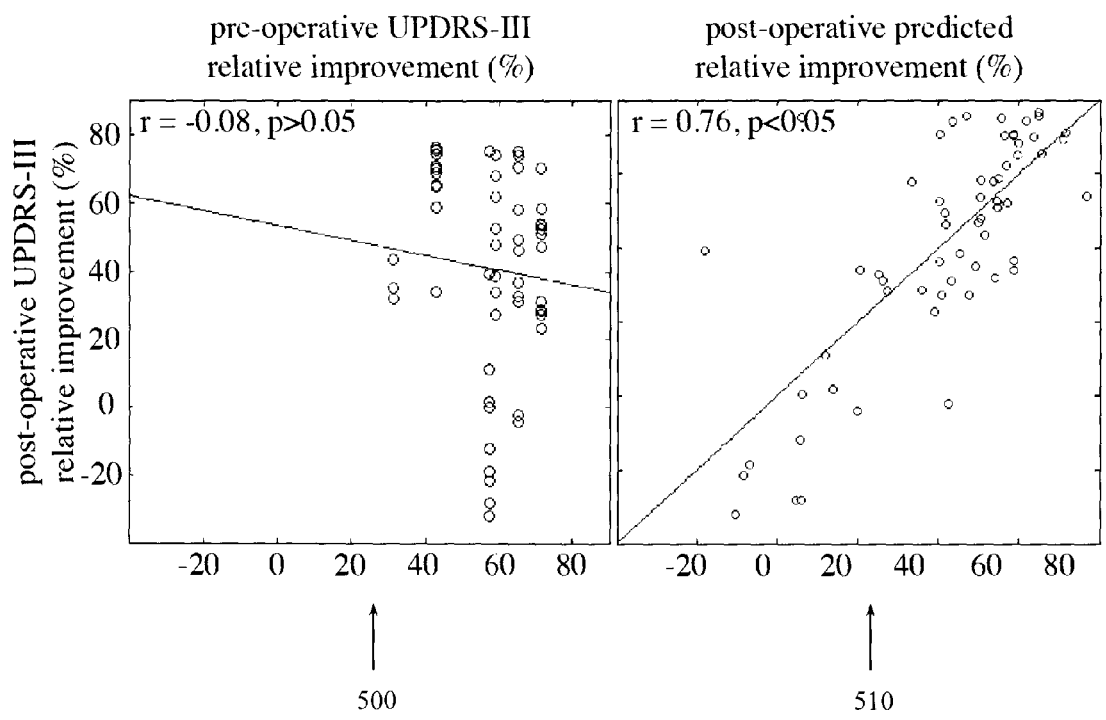
FIG. 5 illustrates a comparison of a preoperative UPDRS-III and an example linear predictive function.

To evaluate example ngCDSS, correlations of candidate predictors and actual outcomes were computed. o compare specific symptom improvement for PD patients, the UPDRS-III (motor) section was broken up into composite symptom scores including speech (section 18; max 4), tremor (sections 20-21; max 28), rigidity (section 22; max 20), limb bradykinesia (sections 23-26; max 32), and axial bradykinesia (sections 19 and 27-31; max 24). For example, FIG. 5 illustrates a comparison of a preoperative UPDRS-III 500 and an example linear predictive function 510.

Figure 6:
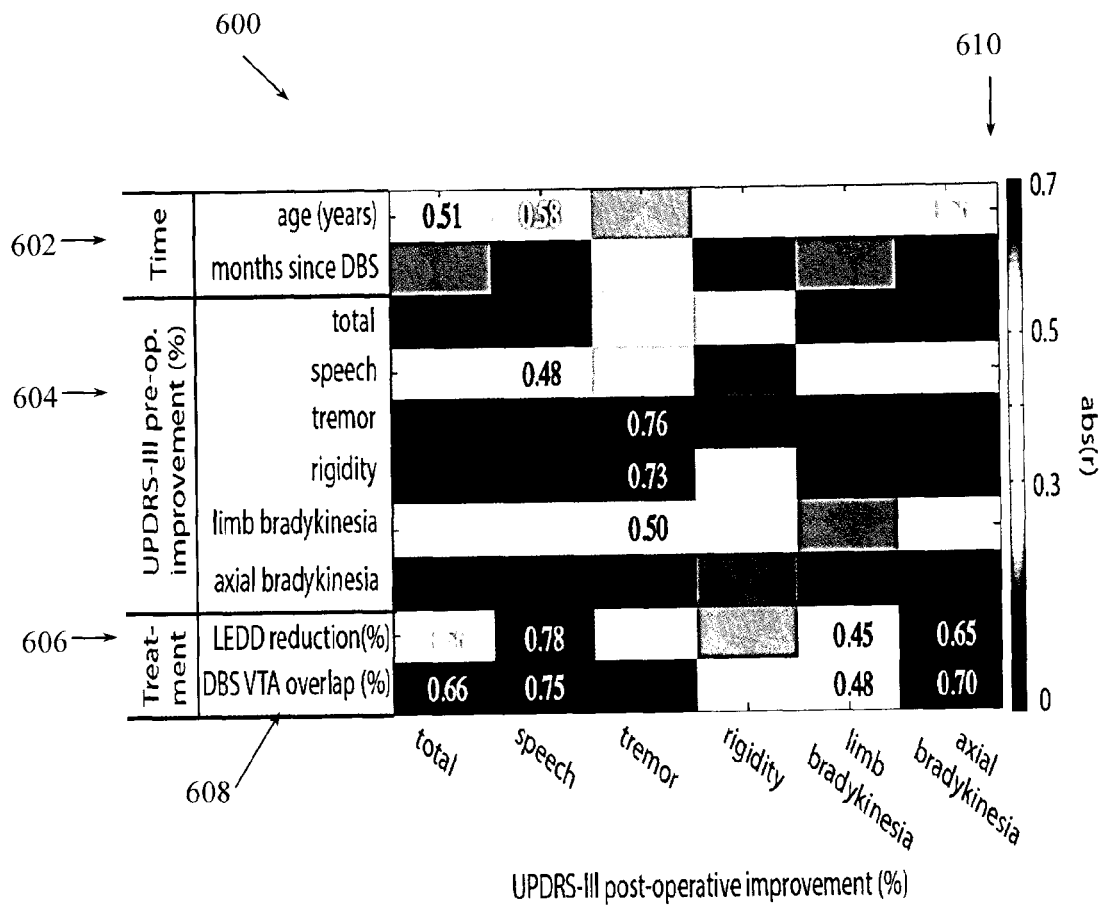
FIG. 6 illustrates a correlation of postoperative DBS treatment outcomes and candidate predictors.

One example set of candidate predictors tested during validation of an example ngCDSS for PD are shown in FIG. 6. Generally, the candidate predictors concern time factors, improvements, and treatments. In one example, the candidate predictors for a PD patient include: patient's age at time of surgery, number of months since surgery at the time of follow-up visit, relative improvement in the preoperative on-medication UPDRS-III total or sub-scores, relative change in LEDD, and mean overlap of ESV and target area over right and left hemispheres. ngCDSS for other types of conditions may have different candidate predictors.

Table 600 correlates post-operative DBS treatment outcomes (columns) and candidate predictors (rows). The predictors include time 602, preoperative motor relative improvement by levodopa 604, relative postoperative LEDD reduction 606, and overlap of ESV with the preferred therapeutic area 608. The absolute values of the correlation coefficients are coded in the bar 610. The correlation numbers were added when the correlation was significant ($p<0.05$; after Bonferroni correction for multiple comparison corrections (MCC)). The UPDRS-III total postoperative improvement is insignificantly correlated with the preoperative relative response to levodopa while LEDD reduction and ESV overlap are significantly correlated with the postoperative improvement of motor symptoms. Improvements in tremor with levodopa in the preoperative tests were significantly correlated with the postoperative relative improvement of tremor. For example, in FIG. 6, $r=0.76$ and $p<0.05$ after MCC.

During validation, example ngCDSS demonstrated that postoperative improvement of specific symptoms was correlated with specific subsets of measures. During validation, example ngCDSS also demonstrated that the overlap of the ESV and the TSA was significantly correlated with the motor improvement. During validation, example ngCDSS also demonstrated that combining motor outcome measures and patient-specific stimulation measures generated a metric that was highly correlated with clinical outcomes. In one embodiment, the metric is computed according to:

$$-11.2m+6.5r-6.2h+2.5o+50.4 \approx \text{motor improvement} \quad [6]$$

where:
m denotes months since surgery;
r denotes rigidity preoperative improvement with levodopa;
h denotes hours since last medication dosage; and
o denotes average right/left overlap of ESV and TSA.

In different embodiments the metric may be computed using other formulae. Additionally, the formulae may adapt over time as additional patient data concerning treatments and outcomes is added.

Multi-linear regression analysis was conducted and regression coefficients were computed to best fit the predictors with actual outcomes for PD patients. The multi-linear regression analysis illustrated that the expected postoperative relative improvement (%) of combined DBS-levodopa treatment for a given patient can be estimated as:

$$\text{UPDRS-III} \approx 0.99a - 0.69m - 0.09u + 0.30l + 1.02d - 28.2 \quad [7]$$

where
a denotes age at surgery,
m denotes months since DBS surgery,
u denotes the preoperative relative response to levodopa as measured with UPDRS-III,
l denotes the postoperative relative change to LEDD values, and
d denotes the overlap between ESV and target area as a result of DBS.

Different formulae that predict expected postoperative relative improvements may be employed for different conditions.

In one validation, fourteen postoperative visits performed approximately one year following DBS surgery were selected as test cases. An example ngCDSS accurately predicted the motor improvement generated by the specific input parameters (e.g., patient data, medication data, stimulation data). In the validation, a leave-one-out approach incorporated known clinical information to train a machine learning classifier. The specific visit being evaluated was left out of the training. The classifier inputs were treated as fixed parameters that are set by the caregiver and the outputs were treatment parameters to be optimized to improve patient outcome. In one validation, the fixed parameters were age, months since surgery, preoperative motor response to levodopa (e.g., UPDRS-III and its subscales), the preoperative levodopa daily dosage, and the ESV/TSA overlap. The treatment parameters were the postoperative LEDD and the medication administration times.

In one validation, the UPDRS-III outcomes from the postoperative visits were classified into three categories. The categories included non-response (e.g., less than 35% improvement after combined DBS and medication therapy with respect to the preoperative off medication state), moderate response (e.g., 35% to 60% improvement), and high response (e.g., greater than 65% improvement). Since preoperative improvement of 30% or more from levodopa alone was an inclusion criterion for DBS surgery, an improvement of 35% or less under the combined treatment presents insignificant benefit to the patient.

In one embodiment, the classification is based on post-operative visits and not by patient. Classification may be post-operative visit based because the same patient may have different symptoms at different times depending on factors including, treatment administered to the patient, medication timing, and disease progression.

In the validation, the classifier was used to predict the expected improvement in the fourteen test cases. The actual clinical outcomes measured for the fourteen cases were compared to example results from different ngCDSS approaches. The different ngCDSS were trained using different machine learning methods including Naïve Bayes classifier (NB; uniform distribution of priors), Support Vector Machine (SVM; with Gaussian radial basis function kernel and least squares method for finding the separating hyperplane), and Random Forest (RF; with ensemble of 50 decision trees).

In the validation, predictions were made not just for an overall motor score, which could misrepresent actual outcomes due to variability among patients, but also for sub-systems. In one embodiment, the sub-system scores were then aggregated into a prediction. This may be referred to as the symptoms aggregate (SA) prediction.

Table 3 illustrates observed prediction accuracies for different machine learning algorithms for PD during one example validation.

TABLE 3

| | Method | | | | |
| --- | --- | --- | --- | --- | --- |
| Symptom | SVM | NB | RF | Consistent prediction | Symptoms aggregate |
| Overall motor | 71% | 64% | 64% | 88% | 86% |
| Speech | 93% | 64% | 86% | NA | NA |
| Tremor | 100% | 64% | 100% | NA | NA |
| Rigidity | 57% | 57% | 50% | NA | NA |
| bradykinesia (limbs) | 78% | 71% | 86% | NA | NA |

The direct prediction accuracies for the overall motor outcomes were 71%, 64%, and 64% using the SVM, Naïve Bayes, and RF methods respectively. Higher accuracies were observed for some specific symptoms. For example, tremor and speech outcomes were predicted with accuracies of 100% and 93% for the SVM method. The limb bradykinesia and axial akinetic symptoms were predicted with accuracy of 86% using the RF classifier. Predicting the overall motor outcomes as a weighted sum of the individual symptom predictions using the best method for each symptom, which is referred to as the SA method, improved prediction accuracy to 86%.

Figure 8:
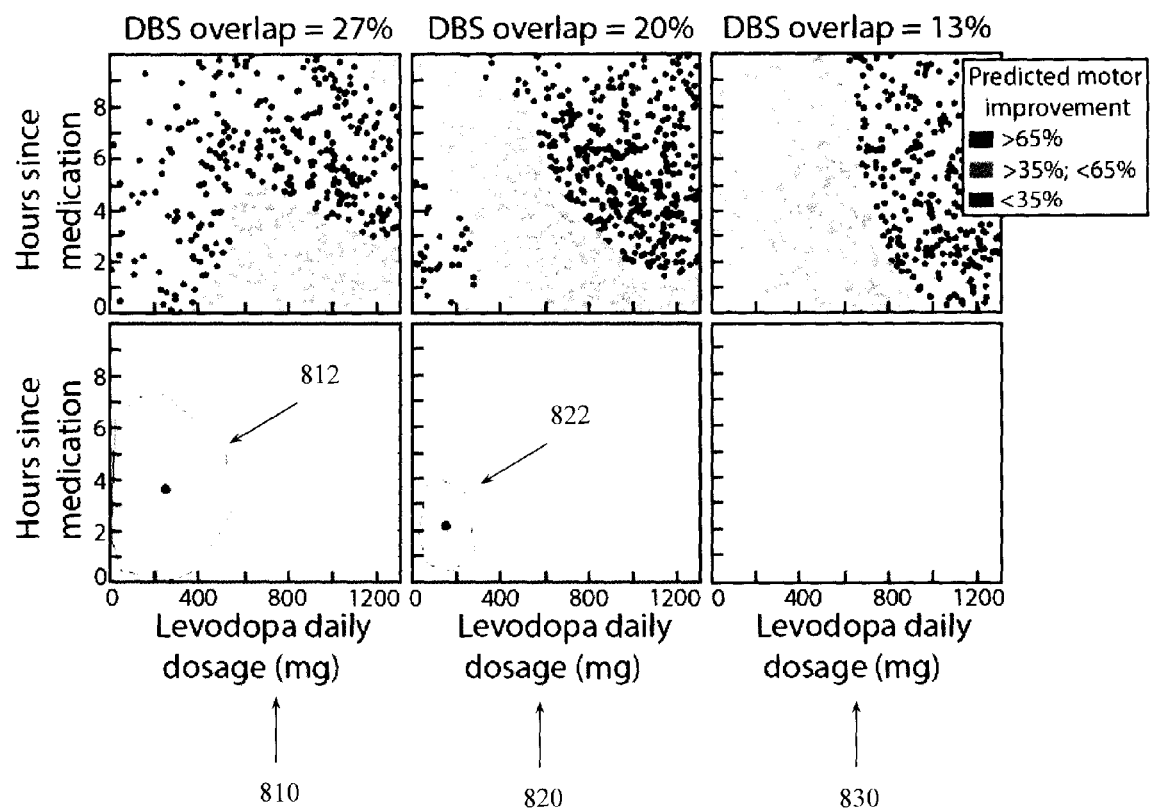
FIG. 8 illustrates a visualization of treatment outcomes and recommended treatments.

An example ngCDSS may produce an output like that illustrated in FIG. 8. The ngCDSS may use a classification tool to broadly sample the complex parameter space of different medication and DBS dosages. An example ngCDSS computes a shape (e.g., convex hull 812, 822) of the treatment parameters that generated a high response prediction. The center of the shape (e.g., 812, 822) is used by the ngCDSS or clinician to provide the recommendation concerning DBS parameters and medication.

An example display also facilitates understanding the mutual interaction between stimulation and medication. For example, the columns in FIG. 8 illustrate these interactions. Simulating various overlap values between the ESV and the TSA alters the predicted optimal medication therapy. Enhancing the overlap between the ESV and the target area is associated with a wider range of effective medication treatments. For example, an overlap of 27% in column 810 produces a wider range of treatment options (as illustrated by convex hull 812) than does an overlap of 20% in column 820 (and convex hull 822), or an overlap of 13% in column 830.

Example ngCDSS use available similarity information to produce a recommendation for a combination of DBS and medication for a current patient. In PD, example apparatus and methods rely on the fact that the combination of relative preoperative response to levodopa, relative change in LEDD, and ESV overlap with TSA are highly correlated with the actual motor outcomes. For other conditions, other correlations may be considered. Unlike conventional systems that may attempt to make a prediction of the outcomes for various treatment strategies based on a single correlation, predictions of the outcomes for multiple correlations of various treatments are made by example apparatus and methods.

Example ngCDSS facilitate selecting medications and DBS parameters for a combined pharmacologic-DBS treatment. The combined pharmacologic-DBS treatment approach may provide superior results because both stimulation and medication parameters appear to be equally important to measured motor outcomes. One example ngCDSS is modelled on the theory that larger ESV/target overlap is associated with increased medication efficacy time.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 9:
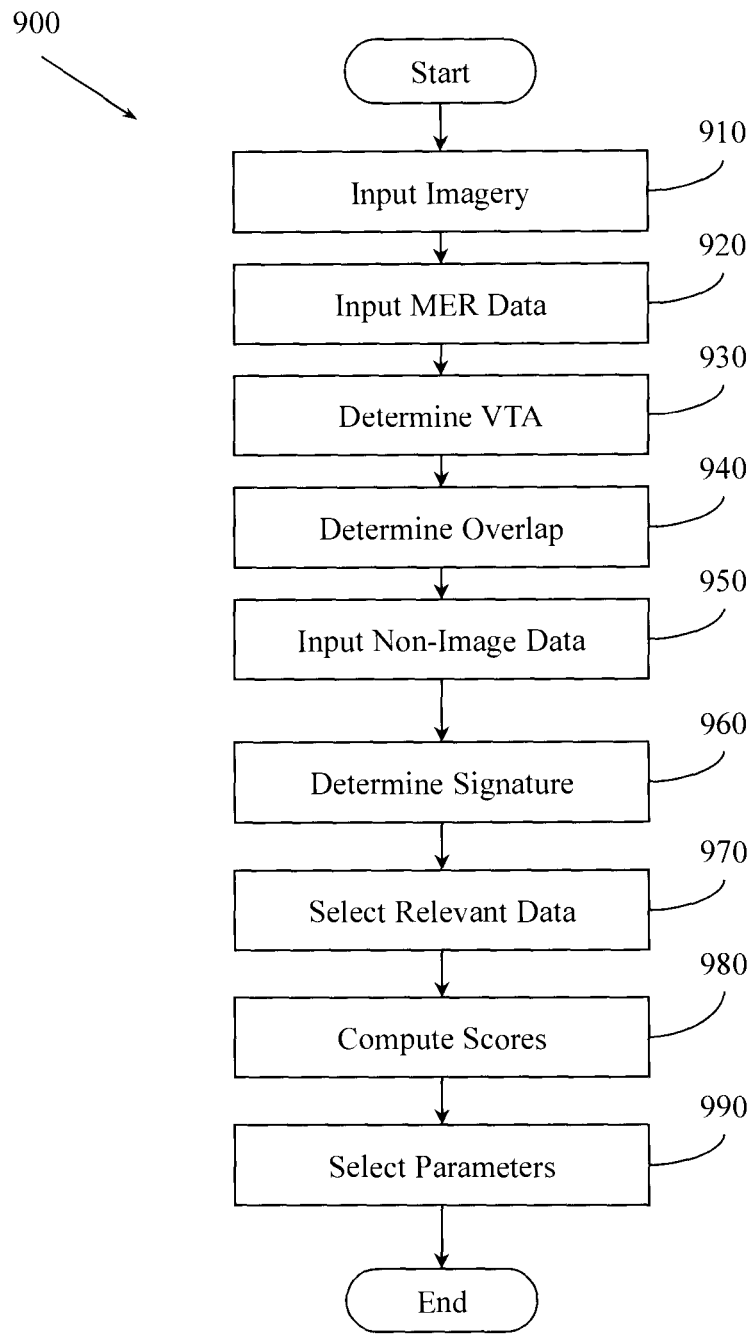
FIG. 9 illustrates an example method associated with an ngCDSS.

FIG. 9 illustrates an example method 900 for selecting DBS stimulation parameters and medication parameters to treat a patient implanted with a DBS system. In one embodiment, the patient may be a PD patient. Method 900 includes, at 910, inputting into a computer a magnetic resonance (MR) image of the brain of the patient and a computed tomography (CT) image of the brain of the patient. In one embodiment, the DBS system includes electrodes located in the subthalamic nucleus of the patient. In different embodiments, the DBS system may include electrodes in the globus pallidus, the pedunculopontine nucleus, or other locations.

Method 900 also includes, at 920, inputting into the computer data from an intraoperative microelectrode recording (MER) performed during implantation of the DBS system. In different embodiments, the MER data may not be acquired. With the MR image, the CT image, and in some embodiments the MER data available, method 900 proceeds, at 930, by controlling the computer to determine a location of an electrode associated with the DBS system and then to determine an estimated stimulation volume (ESV) of tissue stimulated in the brain of the patient based on the location of the electrode. Once the ESV has been computed, method 900 proceeds, at 940, by controlling the computer to determine an overlap of the ESV and a TSA in the brain of the patient.

Method 900 also includes, at 950, inputting into the computer non-image data about the patient. The non-image data may include, for example, tremor data, rigidity data, limb bradykinesia data, speech data, axial akinetic data, LEDD data, the age of the PD patient when the DBS system was implanted, an amount of time since the DBS system was implanted, medication data, data describing motor improvement by levodopa before the DBS system was implanted, and data describing relative LEDD reduction after the DBS system was implanted. The data may also include, for example, data concerning epilepsy (e.g., seizure frequency, seizure type, or seizure focus), psychiatric disorders (e.g., depression symptoms, obsessive-compulsive symptoms, manic symptoms, or bipolar symptoms) or other conditions and symptoms.

Method 900 also includes, at 960, controlling the computer to determine a signature for the patient based on the overlap of the ESV and the TSA, and the data about the patient. In one embodiment, the signature for the patient may be computed according to equation 4.

Once the signature of the patient is available, method 900 then proceeds, at 970, to control the computer to select data associated with other patients based on the signature of the patient. In one embodiment, selecting the data associated with other patients is a function of a similarity score computed according to equation 5.

Method 900 also includes, at 980, controlling the computer to compute scores for three or more attributes of a condition (e.g., PD) for the patient and to compute an aggregate score from the scores for the three or more attributes according to a linear weighted sum function. While three or more attributes are described, in one embodiment method 900 may compute an aggregate score from the scores for two attributes, for four attributes, or for more attributes.

Once the overlap and the aggregate score are available, method 900 concludes, at 990, by controlling the computer to select one or more DBS parameters and one or more medication parameters for treating the patient. The DBS parameters and the medication parameters are selected based on the aggregate score, correlations with the selected data associated with other patients, and the overlap. In one embodiment, the one or more DBS parameters include a stimulation time, a stimulation location, a stimulation duration, a stimulation frequency, and a stimulation amplitude. In one embodiment, the one or more medication parameters include a drug to be delivered, a dose of the drug to be delivered, a time interval at which the drug is to be delivered, and a delivery method for the drug to be delivered.

Figure 10:
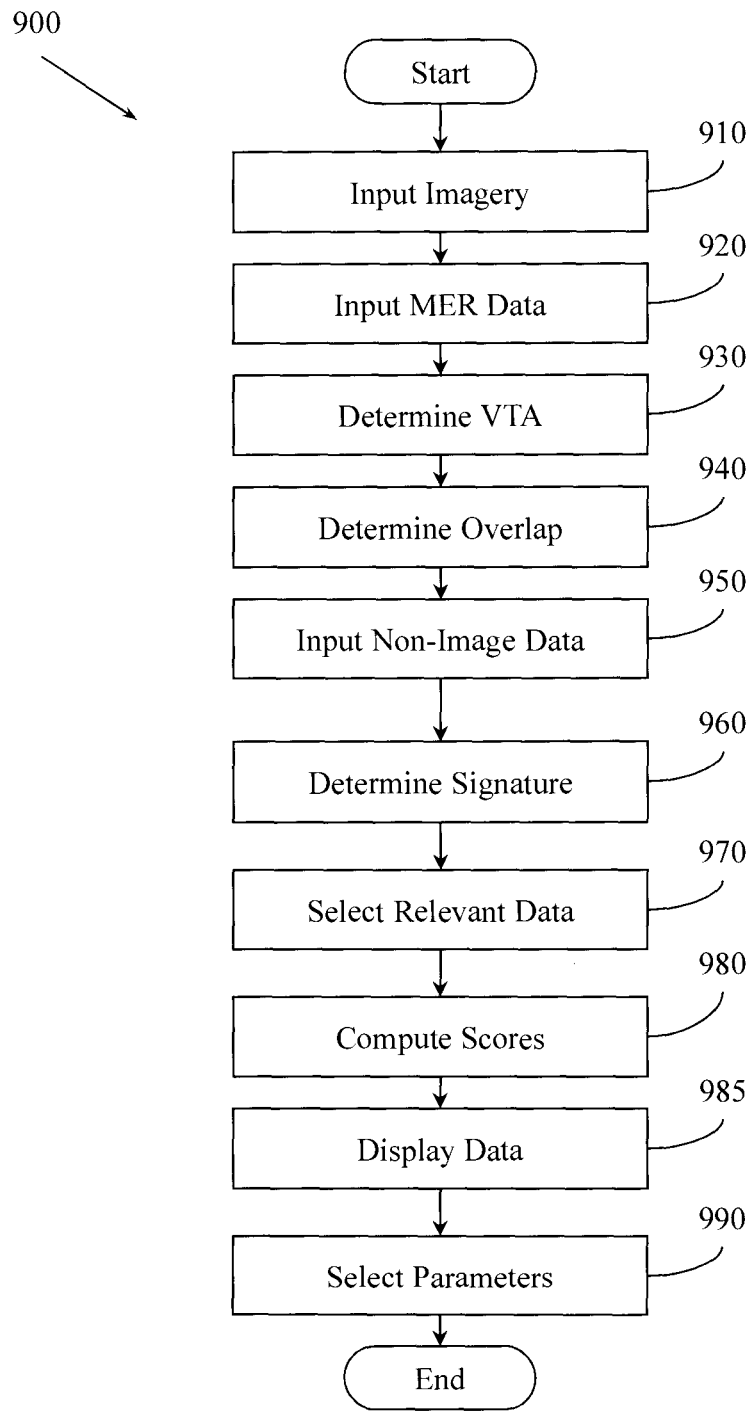
FIG. 10 illustrates an example method associated with an ngCDSS.

FIG. 10 illustrates another embodiment of method 900. This embodiment includes, at 985, controlling the computer to display data upon which the selection of the one or more DBS parameters and the one or more medication parameters is made. In one embodiment, displaying the data includes displaying a geometric shape that covers an area of suitable DBS parameters and suitable medication parameters. The geometric shape may be, for example, a convex hull.

Figure 11:
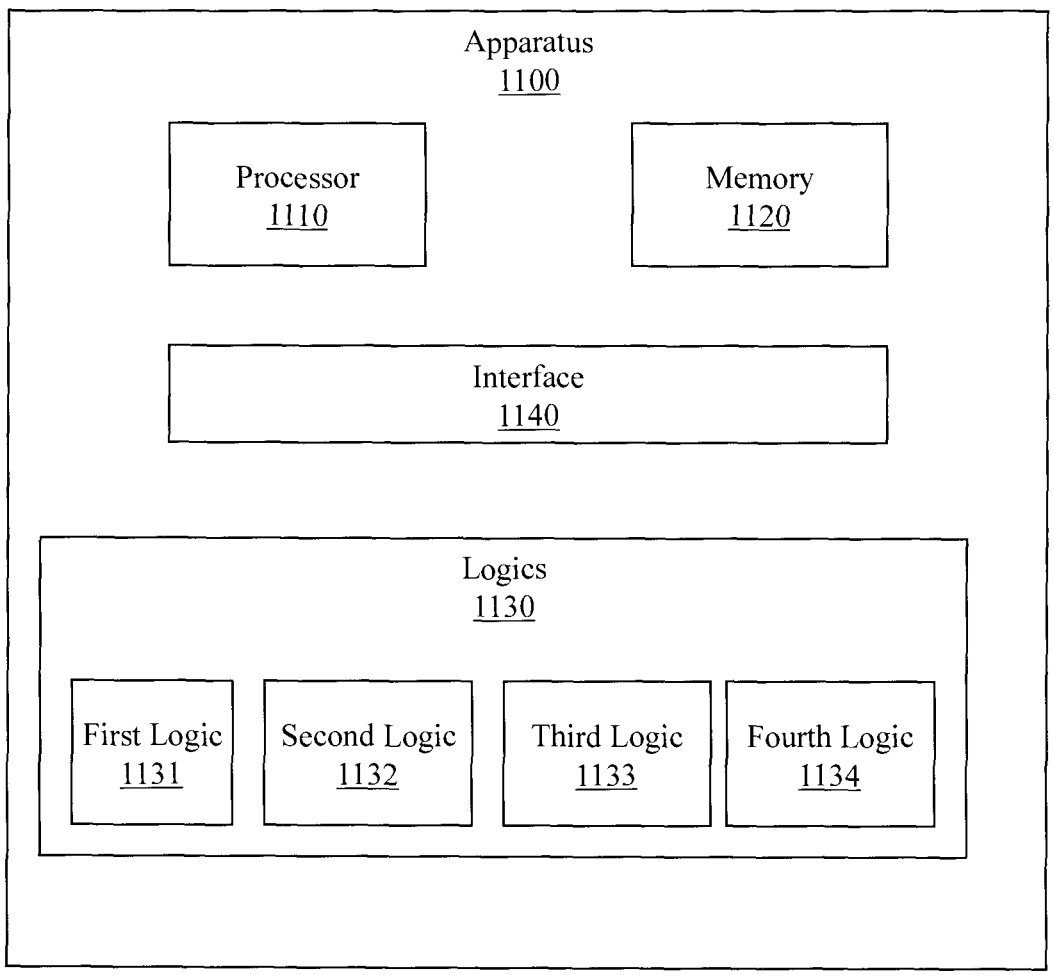
FIG. 11 illustrates an example apparatus associated with an ngCDSS.

FIG. 11 illustrates an example apparatus 1100 that selects treatment parameters for a patient. Apparatus 1100 includes a set of logics 1130 that perform various actions for apparatus 1100. The set of logics 1130 includes a first logic 1131 that produces first electronic data that characterizes a neuroanatomical condition of the patient having a DBS electrode implanted in their brain. The electrode may be, for example, in the subthalamic nucleus, the globus pallidus, the pedunculopontine nucleus, or other regions. The first electronic data may be stored in a memory 1120. In one embodiment, the first logic 1131 characterizes the neuroanatomical condition of the patient based on medical imagery (e.g., MR image, CT image). In one embodiment, the first logic 1131 may also use data acquired from an intraoperative MER performed during implantation of the DBS electrode, however this step may be optional.

In one embodiment, the first logic 1131 determines an overlap between a ESV in the brain of the patient and a target stimulation area (TSA) in the brain of the patient. The TSA may be, for example, an ellipsoid that intersects the dorsal area of the sub thalamic nucleus and the Zona Incerta. In different embodiments, the TSA may intersect different areas including the zona incerta, the globus pallidus, the pedunculopontine nucleus, or other areas.

Apparatus 1100 also includes a second logic 1132 that produces second electronic data that characterizes the patient based on patient symptom data and patient non-symptom data. The second electronic data may also be stored in memory 1120. For PD, the patient symptom data may include, for example, data concerning tremor symptoms, rigidity symptoms, bradykinesia symptoms, speech symptoms, and axial akinetic symptoms. Other patient symptom data may be analyzed for other conditions. For PD, the patient non-symptom data may include, for example, data concerning the age of the patient at the time the DBS electrode was implanted, data concerning an amount of time since the DBS electrode was implanted, data concerning a pre-operative motor improvement produced by levodopa, and data concerning a relative levodopa equivalent daily dosage (LEDD) reduction following implantation of the DBS electrode. Other patient non-symptom data may be analyzed for other conditions.

Apparatus 1100 also includes a processor 1110 that computes a similarity metric for the patient based, at least in part, on the first electronic data and the second electronic data. The processor 1110 may be connected to the set of logics 1130 and the memory 1120 by a hardware interface 1140. In one embodiment, the processor 1110 computes the similarity metric based on the patient symptom data, the non-symptom data, and the overlap between the ESV and the TSA. The processor 1110 may be, for example, a microprocessor in a computer, a specially designed circuit, a field-programmable gate array (FPGA), an application specific integrated circuit (ASIC), a processor in a mobile device, a system-on-a-chip, a dual or quad processor, or other computer hardware.

Once a value for the similarity metric has been determined, a third logic 1133 may identify relevant data associated with a set of other patients and their therapeutic outcomes based on the similarity metric. In one embodiment, the third logic 1133 identifies the relevant data based on a linear weighted sum function applied to data associated with the set of other patients. In one embodiment, the linear weighted sum function is the product of machine learning associated with multi-linear regression analyses that identify correlations in data associated with the set of other patients and their therapeutic outcomes. The machine learning may have included, for example, NB learning, RF of trees learning, and SVM learning. In one embodiment, the linear weighted sum function produces an aggregate score from separate scores for different members of the patient symptom data and the patient non-symptom data. The separate scores for different members of the patient symptom data and the patient non-symptom data may be selected from results produced by different machine learning.

Apparatus 1100 also includes a fourth logic 1134 that produces third electronic data that identifies a combination of treatment parameters for the patient. The fourth logic 1134 may identify the combination of treatment parameters based, at least in part, on the relevant data. The combination of treatment parameters includes one or more DBS parameters and one or more medication parameters.

Figure 12:
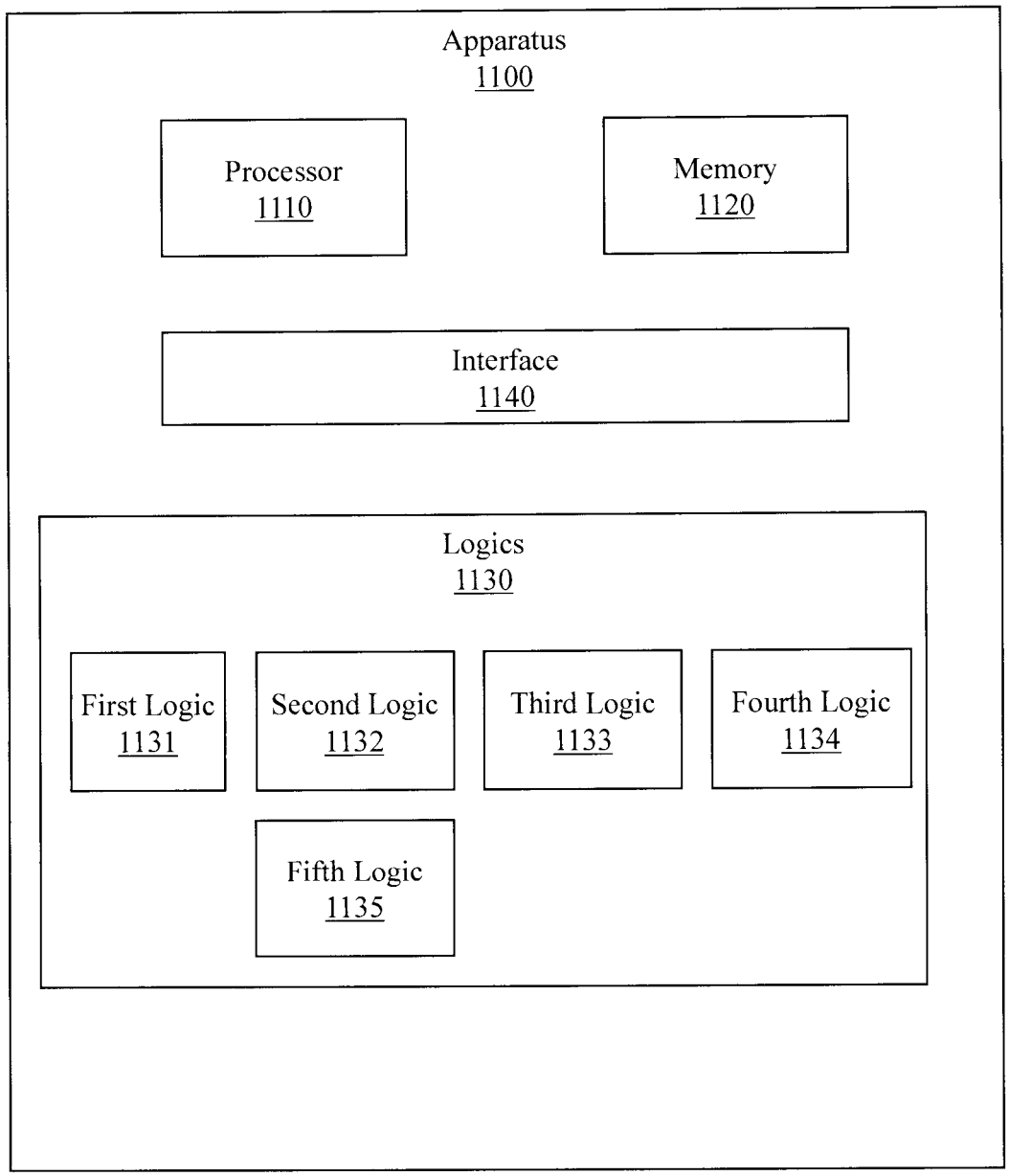
FIG. 12 illustrates an example apparatus associated with an ngCDSS.

FIG. 12 illustrates another embodiment of apparatus 1100. This embodiment includes a fifth logic 1135 that provides a visualization of the relevant data from which the fourth logic 1134 selects the combination of treatment parameters. The visualization may take the form of a geometric shape or volume that covers a subset of treatment parameters associated with favorable outcomes for other patients.

In one embodiment, the functionality associated with the set of logics 1130 may be performed, at least in part, by hardware logic components including, but not limited to, FPGAs, ASICs, application specific standard products (ASSPs), SOCs, or complex programmable logic devices (CPLDs).

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for selecting treatment parameters for a patient, comprising:
    a first circuit that produces first electronic data that characterizes a neuroanatomical condition of the patient, where the characterization of the neuroanatomical condition is based, at least in part, on an electrode implanted in a brain of the patient;
    a second circuit that produces second electronic data that characterizes the patient based on patient symptom data and patient non-symptom data;
    a processor that computes a similarity metric for the patient based, at least in part, on the first electronic data and the second electronic data;
    a third circuit that identifies relevant data associated with a set of other patients and their therapeutic outcomes based on the similarity metric;
    a fourth circuit that produces third electronic data identifying a combination of treatment parameters for the patient based, at least in part, on the relevant data, where the combination of treatment parameters includes one or more stimulation parameters and one or more medication parameters; and
    a fifth circuit that provides a visualization, to a display, of the relevant data from which the fourth circuit selects the combination of treatment parameters.

2. The apparatus of claim 1, where the first circuit characterizes the neuroanatomical condition of the patient based on a magnetic resonance image.

3. The apparatus of claim 2, where the first circuit determines an overlap between an estimated stimulation volume (ESV) in the brain of the patient and a target stimulation area (TSA) in the brain of the patient.

4. The apparatus of claim 3, where the processor computes the similarity metric based on the patient symptom data, the non-symptom data, and the overlap between the ESV and the TSA.

5. The apparatus of claim 1, where the third circuit identifies the relevant data based on a linear weighted sum function applied to data associated with the set of other patients.

6. The apparatus of claim 5, where the linear weighted sum function is the product of machine learning associated with multi-linear regression analyses that identify correlations in data associated with the set of other patients and their therapeutic outcomes.

7. The apparatus of claim 6, where the machine learning includes naïve Bayesian (NB) learning, random forest (RF) of trees learning, and support vector machine SVM learning.

8. The apparatus of claim 7, where the linear weighted sum function produces an aggregate score from separate scores for different elements of the patient symptom data and the patient non-symptom data.

9. The apparatus of claim 8, where the separate scores for different elements of the patient symptom data and the patient non-symptom data are selected from results produced by different machine learning approaches.

* * * * *